United States Patent [19]

Rohr

[11] Patent Number: 4,608,978

[45] Date of Patent: Sep. 2, 1986

[54] METHOD AND APPARATUS FOR PHOTOEPILTION

[75] Inventor: Carol B. Rohr, Lincolnwood, Ill.

[73] Assignee: Carol Block Limited, McHenry, Ill.

[21] Appl. No.: 535,857

[22] Filed: Sep. 26, 1983

[51] Int. Cl.[4] .................................... A61N 5/00
[52] U.S. Cl. .......................... 128/303.1; 128/355; 128/398
[58] Field of Search ............. 128/303.1, 395–398, 128/305, 303.18, 907

[56] References Cited

U.S. PATENT DOCUMENTS

| | | | |
|---|---|---|---|
| 3,693,623 | 9/1972 | Harte et al. | 128/398 X |
| 4,309,998 | 1/1982 | Aron et al. | 128/395 X |
| 4,321,926 | 3/1982 | Roge | 128/303.18 |
| 4,388,924 | 6/1983 | Weissman et al. | 128/398 X |
| 4,408,617 | 10/1983 | Augusta | 128/907 X |

FOREIGN PATENT DOCUMENTS

| | | | |
|---|---|---|---|
| 2820903 | 11/1978 | Fed. Rep. of Germany | 128/303.1 |
| 2371935 | 6/1978 | France | 128/395 |

Primary Examiner—Lee S. Cohen

Attorney, Agent, or Firm—Silverman, Cass & Singer

[57] ABSTRACT

The certain quantity of light energy sufficient to effect lifelessness in each of a particular type of hairs, such as is found in a face, arm or back, is provided to the tip of a hand held probe each time a switch is closed, independent of the duration of the switch closure. This relieves the electrologist from having to manually count times, or the number of pulses of light energy applied to a hair body, to effect lifelessness therein. Such counting has been a major part of the photoepilation procedure, and a burden on the electrologist's faculties. In one embodiment, actuating a foot switch provides a series of timed and spaced pulses of light energy for a period, which is selectable by rotating a wiper of a variable resistor-capacitor circuit. The sum of the energies of the pulses over the selected period equals the certain quantity of light energy. In another embodiment, depressing one of four foot switches provides one of four fixed periods of light pulses. In both embodiments, the certain quantity of light energy is first determined for the hair type and then that certain quantity is used for all the hairs of that type to be removed.

10 Claims, 4 Drawing Figures

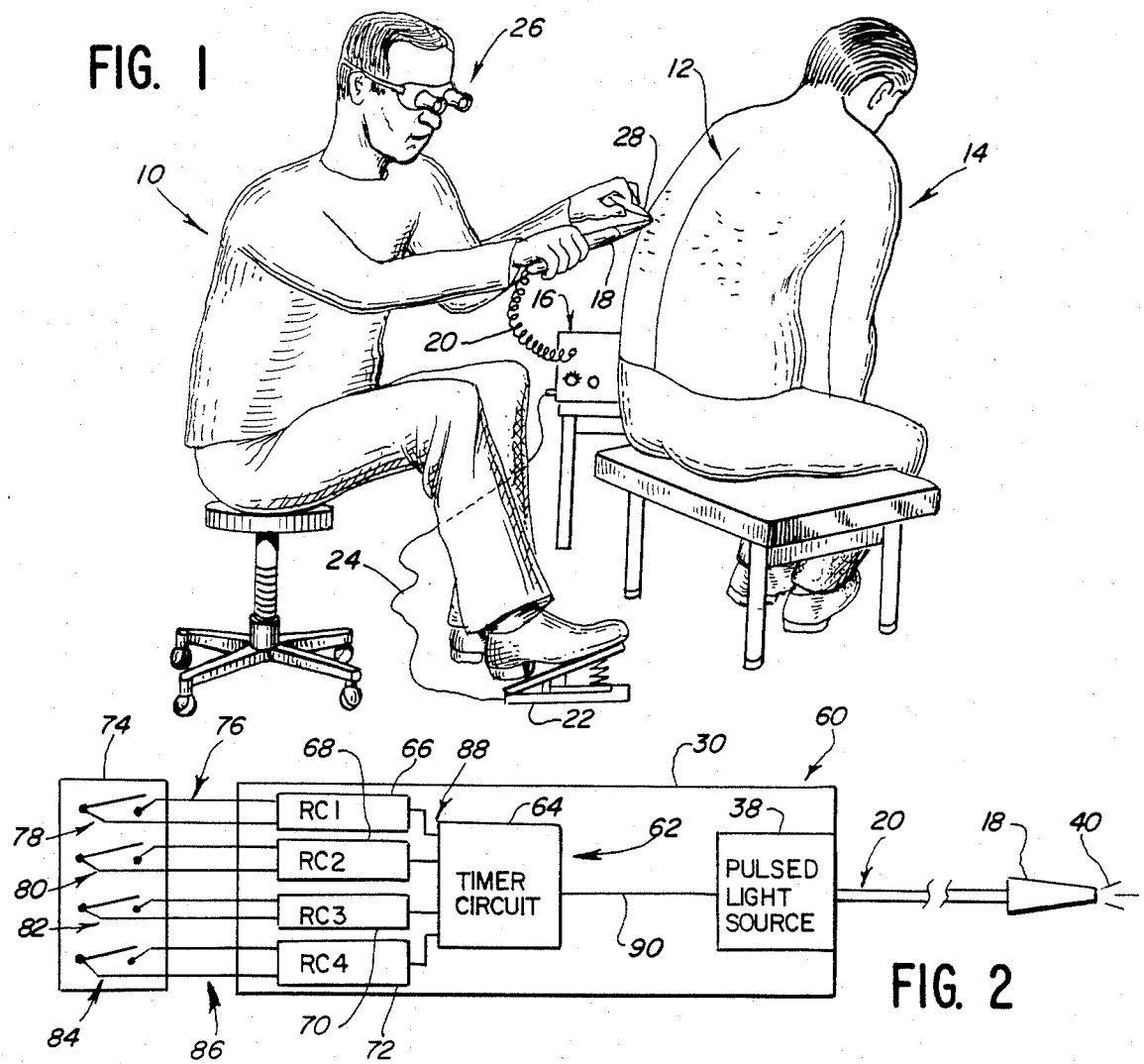
FIG. 1
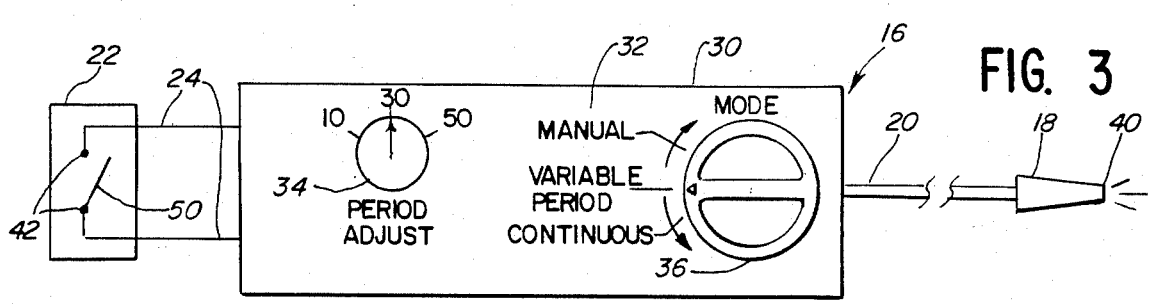
FIG. 2
FIG. 3
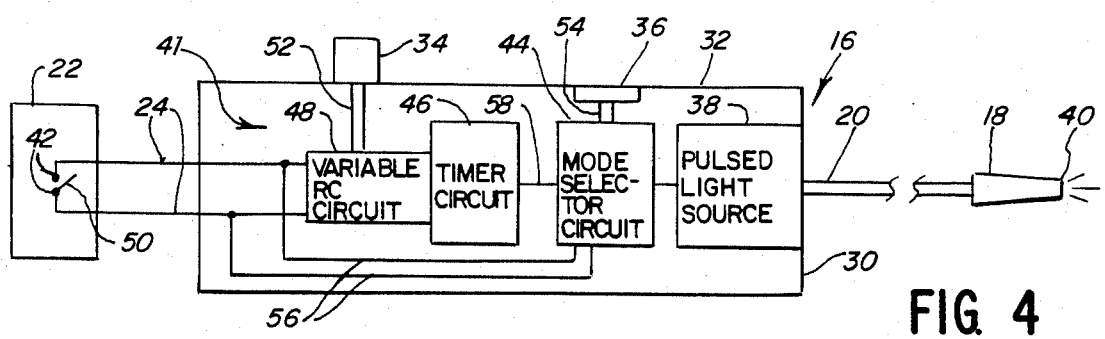
FIG. 4

METHOD AND APPARATUS FOR PHOTOEPILTION

BACKGROUND OF THE INVENTION

This invention relates to epilation primarily for cosmetic and medical purposes, and specifically relates to an improved method of performing photoepilation and an apparatus for performing the method.

Photoepilation is the removal of hair using light energy and is a known, commercially available process. It is performed to obtain cosmetically more pleasing skin by removal of unsighty hair from locations such as the face, legs, arms and back.

It is performed by an electrologist or operator seatedy opposite a patient and specifically opposite an exposed area of the patients skin on which the epilation is to be performed. The operator uses a magnification means such as wearing extended loupe eye glasses to sight on the hair follicles, and in one hand holds a light probe while in the other hand holds a tweezers, for removal of the hairs from the follicles after application of the light probe. The light probe is the termination of a flexible optical means, such as a bundle of optical fibers, that carry light energy to the hair follicle from a discharge lamp contained in a housing of a photoepilation device. The device includes the probe, the housing and a foot switch, which the operator depresses to control of the number of light pulses to be provided by the device.

Performing the photoepilation is demanding of the operator's mental and physical faculties. The operator focuses his or her eyes on one hair and its follicle by looking through the extended loupe eye glasses, moves his or her head to the proper distance from the hair to obtain a sufficient magnification and/or clear focus and then holds his or her head still to maintain the desired sight of the follicle. The operator then moves the tip of the probe, which sources the light energy, to the hair follicle and positions it for applying properly the light energy to the hair follicle. The operator then depresses his or her foot on the foot pedal to close the switch therein and energize the photoepilation device, providing the light energy in timed and spaced pulses. The number of pulses, or the time (which is proportional to the number of pulses) is counted by the operator either out loud or privately to apply the proper quantity of light energy to the hair follicle to effect lifelessness therein. When the proper quantity of energy has been applied to the hair to kill the hair body or root, the operator lifts his or her foot from the foot pedal to stop production of the light energy, and removes the hair from the follicle with the tweezers held in his or her other hand. The operator then moves to the next hair to be removed and repeats this entire demanding procedure.

The quantity of light energy produced by the device is regulated or dependent entirely and solely upon the length of time that the operator depresses the foot pedal of the switch assembly.

The electrologist, thus, to remove one hair, must have excellent motor skills to coordinate simultaneous movement of his or her head and eyes, both hands and one foot. Further, this procedure is tiring because of the physical and mental demands placed upon the electrologist to perform for extended periods.

It is desirable to alleviate at least one of the demands made of the electrologist.

SUMMARY OF THE INVENTION

The invention revolves around providing a proper or certain quantity of light energy at the tip of a probe sufficient to effect lifelessness in a hair body upon the closure of a pair of switch contacts, independent of the duration of the closure of the switch contacts. The quantity of light energy is provided in the form of incremental flashes or pulses of light energy, each of which having a light energy quantity equal to the others, but less than the proper quantity. The pulses are provided in like, timed and spaced relation to one another so that providing a series of the pulses for a selected duration period provides the proper quantity of light energy. In effect, the sum of the energies of the light pulses provided in the selected period equals the proper quantity of light energy to effect the lifelessness.

The demands upon the electrologist are alleviated by the electrologist selecting the period by setting the period duration to obtain the proper quantity of light energy to effect the lifelessness in a particular type of hair located on such as a face, an arm or a back. Then for each hair of the type, the electrologist need only actuate a switch once to obtain the proper quantity of light energy. The duration of the actuation of the switch need not be precisely regulated by the electrologist because the duration of the selected period is independent of the duration of switch closure.

The apparatus of the invention comprises a flash lamp and control circuit assembly, a hand held probe connected to the flash lamp by a bundle of flexible, optical fibers and a foot switch assembly electrically connected to the control circuit by a cable. The control circuit is operable, in reaction to actuation of the foot switch, to flash the lamp in timed and spaced pulses of equal light energy.

In one embodiment, the foot switch assembly comprises a plurality of switches, one switch for each of a plurality of fixed periods. Selecting the certain period then comprises placing the operator's foot above the switch corresponding to the quantity of light energy required to effect the lifelessness in the type of hair to be removed from the subject patient. In another embodiment, the control circuit includes a variable timer for selecting the certain period and the foot switch assembly comprises one switch for commencing the period. Selecting the period thus comprises moving the wiper of a variable resistor or capacitor to a particular setting.

BRIEF DESCRIPTION OF THE DRAWING

FIG. 1 depicts a scene in which an electrologist is performing a photoepilation procedure upon the hairs on the back of a patient;

FIG. 2 is a block diagram of the one embodiment of the apparatus of the invention;

FIG. 3 is a front side view of another embodiment of the apparatus of the invention; and FIG. 4 is a block diagram of the other embodiment of the apparatus of the invention.

DESCRIPTION OF THE PREFERRED EMBODIMENT

In FIG. 1, an electrologist or operator 10 is removing hair from the back 12 of a patient 14 using a proximately located photoepilation apparatus indicated generally by the reference character 16. Apparatus 16 comprises a probe 18 held in the right hand of electrologist 10 and an optical cable 20 connecting the probe 18 to the apparatus 16. Optical cable 20 comprises flexible optical transmission means such as optical fibers. Apparatus 16 further includes a foot switch assembly 22 connected thereto by an electrical cable 24. Assembly 16 is operatively located under the right foot of the electrologist. FIGS. 3 and 4 illustrate the embodiment of apparatus 16. The electrologist 10 comfortably is seated opposite the bare back 12 of the seated patient 14. The electrologist 10 wears an extended loupe carrying eyeglasses 26 better to see the hair follicles on the patient's back 12 and holds a tweezers 28 in his or her left hand for removing lifeless hairs.

Typically all of the hairs or hair bodies to be removed from one region of a person's skin, such as face, arms, back, legs, are of one to three types, and the light energy that must be applied to each hair of one type to effect lifelessness therein is constant. Thus, once a particular quantity of light energy to effect lifelessness is established for a hair type, that quantity need only be repeatedly supplied to each hair root to perform the photoepilation.

In FIGS. 3 and 4, apparatus 16 includes a box-like housing or container 30 providing a face plate 32 on which are located a PERIOD ADJUST knob 34 and a MODE CONTROL knob 36. Interior of container 30, a pulsed light source 38, including a flash lamp, produces or sources light energy through an optical cable 20 to probe 18. The light energy is output from the tip 40 of the probe. A foot switch assembly 22, having one pair of normally open contacts 42 is connected to the apparatus by electrical cable 24. A control circuit 41, comprising mode selector circuit 44, timer circuit 46 and variable RC circuit 48, operate generally to produce timed and spaced pulses of light energy in source 38, and thereby to probe tip 40. Mode selector circuit 44 determines whether the flash lamp will be operated, in one of three modes: manually, for a period of time commencing and ending respectively with the closing and opening of contacts 42 by wiper or foot pedal 50; for a variable period commencing with the closing of contacts 42 by foot pedal 50 and extending for a duration determined by the setting of the variable RC circuit by knob 34 through shaft 52; and continuously for a period of time commencing with the closing of contacts 42 by foot pedal 50 and ending with a second closing of contacts 42 by foot pedal 50. In all cases, contacts 42 are closed by electrologist 10 depressing his or her foot on foot pedal 50 and are opened by the technologist raising his or her foot from the foot pedal. Rotation of knob 36 through shaft 54 effects selection of the desired mode.

In the manual and continuous modes, closing of contacts 42 is conducted to mode control circuit 44 by wires 56 from cable 24. In the variable period mode, cable 24 directly carries the signal indicating closing of contacts 42 to variable RC circuit 48 and timer circuit 46. Timer 46 then produces a signal on wire 58 to selector 44 that has a period corresponding to that indicated by knob 34. In all three cases, mode selector circuit 44 includes a circuit to energize light source 38 and obtain regular timed and spaced pulses of light therefrom. The timing and spacing of the pulses is fixed to obtain equal but incremental quantities from each pulse of light energy. The only variable afforded by the control circuit 41 thus is the number of pulses or incremental quantities of light energy sourced to probe tip 40. The control circuit 41 does not count the number of pulses but provides them for a selected period.

In operation, the electrologist selects the variable period mode by rotating knob 36 and selects a certain period corresponding to the quantity of light energy, in the form of the timed and spaced pulses, required to be sourced at the tip 40 to effect lifelessness in a particular type of hair body. Selection occurs by rotation of knob 34 to vary the resistance or capacitance of circuit 48. The electrologist then adjusts his or her head to sight on one hair follicle, properly places the probe tip 40 in the vicinity of the follicle and depresses the foot pedal wiper 50 once. The control circuit then automatically, and independently of the length of time that the contacts 42 are closed, causes a series of timed and spaced pulses of light energy, for the selected period, to be sourced to the probe tip 40, and therefrom to the hair body to effect lifelessness therein. The electrologist then removes the lifeless hair body from the follicle, and moves to the next follicle, repeating the described procedure.

The method and apparatus of the invention thus relieve the electrologist from the manual counting of time or pulses to effect the lifelessness with the light energy. The termination of the selected period is seen by the electrologist by the lack of light pulses being supplied to the follicle from the probe tip. Operation in the manual and continuous mode is similar to that described in the previous paragraph but requiring a different actuation of the foot pedal 50 for each respective mode.

In FIG. 2, a second embodiment of the photoepilation apparatus of the invention is indicated generally by reference character 60. The same reference characters indicate the same elements in FIGS. 2, 3 and 4.

Apparatus 60 comprises container 30, optical cable 20, probe 18, probe tip 40 and pulsed light source 38 previously described. A control circuit 62 includes a timer circuit 64, four resistor-capacitor networks RC1-RC4, respectively, 66–72, a switch assembly 74 and an electrical cable 76. Assembly 74 provides four, normally open pairs of contacts or switches 78–84. Switches 78–84 are mounted on a panel for operation by the electrologist—s foot and may be such as push button switches. Four pairs of wires 86 connect the contacts of each switch to its respective resistor-capacitor circuit, these wire pairs forming cable 76. In turn, each resistor-capacitor circuit 66–72 is connected to timer circuit 64 by four separate wires 88. Timer circuit 64 is connected to light source 38 by wire 90.

Control circuit 62 provides four fixed and individually selectable periods of production of the light energy pulses from light source 38 corresponding to the four switches 78–84. Switch 84 provides a period of (15) minutes, switch 82 provides a period of ten (10) seconds, switch 80 provides a period of thirty (30) seconds and switch 50 provides a period of fifty (50) seconds.

Actuating any one switch 78–84 energizes the corresponding resistor-capacitor circuit and causes timer circuit 64 to produce pulsing signals on wire 90 for the selected period. The pulsing signals on wire 90 cause the flash lamp in light source 38 to flash at regular timed and spaced intervals for the period, provding equal energy light energy pulses at probe tip 40.

The photoepilation procedure performance with apparatus 60 is similar to the procedure performance with apparatus 16, except there is no setting of a mode or period. Instead, selecting a certain period occurs by selecting the desired foot actuated push button switch, which then is depressed to source the required quantity of light energy at the probe tip. Sourcing the light energy pulses is independent of the length of time that the selected switch is actuated.

Selection of the period or energy necessary to effect lifelessness in a particular type of hair is by experiment or otherwise as desired.

Known timing circuits, including monostable multivibrators, can provide the period signals in an apparatus 60. One circuit may provide each fixed period or one circuit may provide all four fixed periods. A known timing circuit, such as a monostable multivibrator can provide the single variable period circuit in apparatus 16. In either case, a circuit such as a monostable multivibrator or one shot, provides a timing signal having a period independent of the switch closure or actuation time. This frees the electrologist from the requirement of having to regulate or control, by counting, the light energy applied to each hair body.

Modifications and variations of the present invention are possible in light of the above teachings. Different control, and timing circuits and switch arrangements and locations can be provided. It is therefore to be understood that within the scope of the appended claims, the invention may be practiced otherwise than as specifically described.

I claim:

1. A method of photoepilation of a plurality of hair bodies of at least one type from a patient, comprising:
   A. providing an apparatus having a flash lamp that sources light energy to the tip of a probe, and a control circuit including means for providing pulses of electrical energy to said flash lamp for causing the lamp to flash to obtain sequential, like, timed and spaced incremental pulses of light energy, the control circuit including a manually actuable switch assembly for energizing the control circuit to provide said pulses of electrical energy and said pulses of light energy for a selectable period, the length of the period being indpendent of the length of time of actuation of the switch assembly;
   B. selecting a certain period corresponding to the proper quantity of light energy in the form of timed and spaced pulses to be sourced at said tip to effect lifelessness in said particular type of hair body;
   C. placing said tip properly in the vicinity of a hair to be removed;
   D. actuating said switch assembly for a length of time independent of said period; and
   E. repeating said steps C and D for said plurality of hair bodies,
   F. so that once the certain period is selected, said proper quantity of light energy automatically is provided to said probe tip independent of the length of time that said switch assembly is actuated.

2. The method of claim 1 including providing the control circuit with a timer circuit that is variable, and said selecting a certain period including varying the timer circuit.

3. The method of claim 2 including providing the timer circuit with a resistor-capacitor circuit variable by manually operable means and said selecting including manually varying the resistor-capacitor circuit.

4. The method of claim 1 including providing the control circuit with a plurality of manually actuable switches, each switch for energizing the control circuit for a respective period of fixed duration, and said selecting a certain period including selecting a certain switch to be actuated.

5. The method of claim 4 including providing the control circuit with a timer circuit and a plurality of fixed resistor-capacitor circuits, connected to the timer circuit, that are independently selectable by a respective one of the plurality of switches, and when selected, each fixed resistor-capacitor circuit determining the duration of one of the periods of the timer circuit.

6. An apparatus for performing photoepilation, comprising:
   a flash lamp source of light energy;
   optical cable means, terminating at a tip of a hand held probe, for conducting light energy from said source to said tip;
   control circuit means connected to said source which, when energized, generates pulses of electrical energy which are transmitted to said source, causing the source to flash and provide sequential, like, timed and spaced, incremental pulses of light energy, said control circuit means including a manually actuatable switch assembly for energizing the control circuit means for a selectable period, the length of the period being independent of the length of time of actuation of the switch assembly, said selectable period being of such duration that the sum of the energies of the incremental pulses of light are proper to effect lifelessness in a hair body.

7. The apparatus of claim 6 in which said control circuit means include a timer circuit and a connected variable resistor-capacitor circuit, the timer circuit providing a period signal having a duration corresponding to the set variation of the resistor-capacitor circuit, the switch assembly including one switch with normally open contacts, which when closed commence the period signal.

8. The apparatus of claim 7 in which said control circuit means include a mode selector circuit used to select at least the period signal of said timer circuit to determine said selectable period.

9. The apparatus of claim 6 in which said control circuit includes at least one timer circuit connected to a plurality of fixed resistor-capacitor circuits, when selected, each fixed resistor-capacitor circuit causing the timer circuit to produce a period signal of respective fixed duration, the switch assembly including one switch connected to only one fixed resistor-capacitor circuit, so that one fixed duration period signal results from actuating one switch.

10. The apparatus of claim 9 in which there are four switches, four fixed resistor-capacitor circuits and one timer circuit.

* * * * *